United States Patent [19]
Kanamori

[11] Patent Number: 5,232,081
[45] Date of Patent: Aug. 3, 1993

[54] SAMPLER FOR MANY SAMPLES AND SAMPLE RACK START/STOCK UNIT

[75] Inventor: Shigeo Kanamori, Mikishi, Japan

[73] Assignee: Toa Medical Electronics Co., Ltd., Kobe, Japan

[21] Appl. No.: 734,789

[22] Filed: Jul. 23, 1991

[30] Foreign Application Priority Data

Sep. 25, 1990 [JP] Japan ................................. 2-254692

[51] Int. Cl.⁵ .............................................. B65G 25/00
[52] U.S. Cl. ............................. 198/465.2; 198/465.1; 198/347.1
[58] Field of Search .................. 198/347.1, 347.4, 444, 198/465.1, 465.2, 460, 771

[56] References Cited

U.S. PATENT DOCUMENTS

| | | | |
|---|---|---|---|
| 2,897,772 | 8/1959 | Hunter | 198/465.1 X |
| 2,903,120 | 9/1959 | Thomas | 198/465.2 X |
| 3,221,781 | 12/1965 | Forsstrom | 198/465.2 X |
| 3,351,177 | 11/1967 | Mulligan | 198/465.2 X |
| 3,451,564 | 6/1969 | Haas | 198/465.2 X |
| 4,050,572 | 9/1977 | Armstrong | 198/771 X |
| 4,147,250 | 4/1979 | Schulz | 198/465.2 |
| 4,356,909 | 11/1982 | November et al. | 198/465.2 |
| 4,454,939 | 6/1984 | Kampf et al. | 198/465.2 X |
| 4,687,093 | 8/1987 | Marshall et al. | 198/465.2 |
| 4,823,539 | 4/1989 | Kuckhermann et al. | 198/465.2 X |

FOREIGN PATENT DOCUMENTS

| | | | |
|---|---|---|---|
| 0066720 | 12/1982 | European Pat. Off. | 198/347.1 |
| 3242484 | 3/1984 | Fed. Rep. of Germany | 198/444 |
| 0896425 | 5/1962 | United Kingdom | 198/347.4 |
| 1412911 | 11/1975 | United Kingdom | 198/347.1 |
| 2043013 | 10/1980 | United Kingdom | 198/347.1 |

Primary Examiner—Robert P. Olszewski
Assistant Examiner—James R. Bidwell
Attorney, Agent, or Firm—Jones, Tullar & Cooper

[57] ABSTRACT

A rack start/stock unit 16 comprises a loader 30 for loading sample racks from outside the unit, an accumulator 32 for accumulating plural sample racks, an unloader 34 for sending out sample racks to outside the unit, a first moving structure for moving the sample racks at the loader to the accumulator, a second moving structure 40 for moving the sample racks at the accumulator to the unloader, and a third moving structure 44 for moving the sample racks at the unloader to outside of the unit. A sampler for many samples comprising a rack start yard 10, a conveyor 12, and a rack stock yard 14. The rack start yard 10 and the rack stock yard 14 are composed by connecting a plurality of rack start/stock units 16, respectively. The sample racks are sent from the rack start yard 10 to the conveyor 12 sequentially to be supplied to analyzers, and are then recovered in the rack stock yard 14. A cushion yard 60 composed of at least one rack start/stock unit 16 is installed adjacent the conveyor 12, so that plural sample racks may stay stagnant temporarily.

6 Claims, 8 Drawing Sheets

SAMPLER FOR MANY SAMPLES AND SAMPLE RACK START/STOCK UNIT

BACKGROUND OF THE INVENTION

The invention relates to a sampler for many samples for transporting sample racks to analyzing apparatus such as blood analyzers and smeared sample generators, and a sample rack start/stock unit for use in this sampler.

Feeding devices of sample racks for feeding blood or other samples to analyzers sequentially by conveying sample racks have been hitherto known (for example, Japanese Laid-open Utility Models Sho. 63-141456, and Sho. 63-141458).

In the conventional sample rack feeding devices, only about 20 sample racks can be set at once in the start yard (that is, about 200 samples supposing 10 samples in one rack). The capacity is the same in the stock yard.

Accordingly, when it is desired to process more samples continuously, sample racks must be additionally set, waiting until the start yard is about to be empty. When the stock yard is filled up with sample racks, they must be taken out, which required great labor (when the stock yard is filled up with sample racks, more sample racks cannot be accepted, and the conveying system stops).

It is, however, not a simple matter to increase capacity by widening the start yard and stock yard. This is because the number of necessary racks is different in each facility. That is, one facility may require 60 racks, whereas another may need only 20 (or in the future, 40 racks or 60 racks may be necessary as the number of samples increases).

Conventionally, preparing plural types of a start yard and a stock yard in different numbers of racks, necessary sizes were selected and used from them. That is, the cost was very high because individual cases were satisfied.

Or if either the start yard or the stock yard falls in trouble, the supply system stops, and the samples cannot be measured.

In addition, when connecting plural analyzers differing in treating capacity, the analysis must be done at the processing speed of the analyzer of the slowest processing capacity.

OBJECTS AND SUMMARY OF THE INVENTION

It is therefore primary object of the invention to provide a sampler for many samples capable of setting multiple (more than scores of) samples at once so as to cope with flexibly at low cost, and a rack start-stop unit for use therein.

It is another of the invention to provide a sampler for many samples capable of processing at high speed at the speed of the high speed analyzer, regardless of the processing capacity of the low speed analyzers, if plural analyzers with different processing capacities are connected.

To achieve the above objects, the invention provides, in a preferred embodiment thereof, a sampler for many samples for sequentially sending sample racks from a start yard to a conveyor, feeding to the analyzer, and recovering in a stock yard, which comprises a start yard and a stock yard connecting a plurality of rack start/stock units, wherein each rack start/stock unit comprises a loader for loading sample racks from outside, an accumulator for accumulating plural sample racks being contiguous to the loader, an unloader for sending out sample racks to the outside being contiguous to the accumulator, first moving means for moving the sample racks at the loader to the accumulator, second moving means for moving the sample racks at the accumulator to the unloader, and third moving means for moving the sample racks at the unloader to the outside, in which the start yard and stock yard are composed by serially connecting the rack start/stock units so that the loader of a certain rack start/stock unit may communicate with the unloader of other rack start/stock units.

Moreover, the invention provides a sampler for many samples for sending sample racks sequentially from the start yard to the conveyor, and feeding to plural analyzers, and recovering in the stock yard, wherein plural rack start/stock units are connected to compose a start yard and a stock yard. A cushion yard comprising at least one rack start/stock unit for temporarily keeping and holding plural sample racks is disposed on the way of the conveyor from the start yard to the stock yard, and the rack start/stock unit comprises a loader for loading sample racks from the outside, an accumulator for accumulating plural sample racks being contiguous to the loader, an unloader for sending out sample racks to the outside being contiguous to the accumulator, first moving means for moving the sample racks in the loader to the accumulator, second moving means for moving the sample racks in the accumulator to the unloader, and third moving means for moving the sample racks in the unloader to the outside, and the start yard and stock yard are composed by serially connecting the rack start/stock units so that the loader of a certain rack start/stock unit may communicate with the unloader of other rack start/stock units.

In such a sampler for many samples, when the cushion yard is composed of plural rack start/stock units, the rack start/stock units are serially connected so that the loader of the upstream side rack start/stock unit and the upstream side conveyor communicate with each other, and that the unloader of the downstream side rack start/stock unit and the downstream side conveyor communicate with each other, and moreover that the loader of a certain rack start/stock unit and the unloader of other rack start/stock units may communicate with each other.

The rack start/stock unit for the sampler for many samples according to the invention comprises a loader for loading sample racks from the outside, an accumulator for accumulating plural sample racks being contiguous to the loader, an unloader for sending out sample racks to the outside being contiguous to the accumulator, first moving means for moving the sample racks in the loader to the accumulator, second moving means for moving the sample racks in the accumulator to the unloader, and third moving means for moving the sample racks in the unloader to outside.

In the rack start/stock unit, it is desired to attach push-back means for pushing back a sensor and sample rack to the wall of the unloader.

According to the invention, practically, in both the start yard and the stock yard, two or more rack start/stock units are connected in series, respectively. Besides, the cushion yard comprises at least one rack start/stock unit, and if plural units are used, the rack start/stock units are connected in series.

In the start yard, the sample racks in, the unloader are sent out by the third moving means to the outside (to the conveyor or the loader of the adjacent rack start/stock unit).

Sample racks are sent in from the outside to the loader (the unloader of the start/stock unit), and the sample racks in the loader are moved to the accumulator by the first moving means. The sample racks in the accumulator are moved entirely in the unloader direction by the second moving means. Thereafter, this operation is repeated, and the sample racks are sent out to the conveyor while shifting by one rack each within the start/stock unit and between the start/stock units.

In the stock yard, sample racks are sent into the loader from the outside (the conveyor, or the unloader of the adjacent start/stock unit), and the sample racks of the loader are moved to the accumulator by the first moving means. The sample racks in the accumulator are moved entirely in the unloader direction by the second moving means. The sample racks in the unloader are sent out by the third moving means to the outside (the loader of the adjacent start/stock unit). Repeating this operation thereafter, the sample racks from the conveyor are recovered as moving within the start/stock unit and between the start/stock units.

When the cushion yard is disposed, the operation is as follows. Same as above, the sample racks are sent out from the loader to the conveyor. Before the analyzer, the sample racks are transferred intermittently, and samples are taken for each specimen. The sample racks after sampling are temporarily held and kept in the cushion yard, and are sent out to the conveyor.

Before the analyzers, the sample racks are intermittently transferred, and samples are taken for each specimen.

If the processing capacity of the plural analyzers installed along the conveyor differs, by temporarily keeping and holding the sample racks in the cushion yard, the sample racks may be transferred without having to cause the high speed analyzer to wait.

BRIEF DESCRIPTION OF THE DRAWINGS

FIG. 2 and FIG. 3 are plan views showing an embodiment according to a rack start/stock unit of the invention, in which FIG. 2 and FIG. 3 are drawn in different configuration and direction.

FIG. 5 and FIG. 6 are diagrams for explaining the purpose of installing push-back means, in which

DETAILED DESCRIPTION OF THE PREFERRED EMBODIMENTS

Referring now to the drawings, some of the preferred embodiments of the invention are described in detail below.

Figure 1:
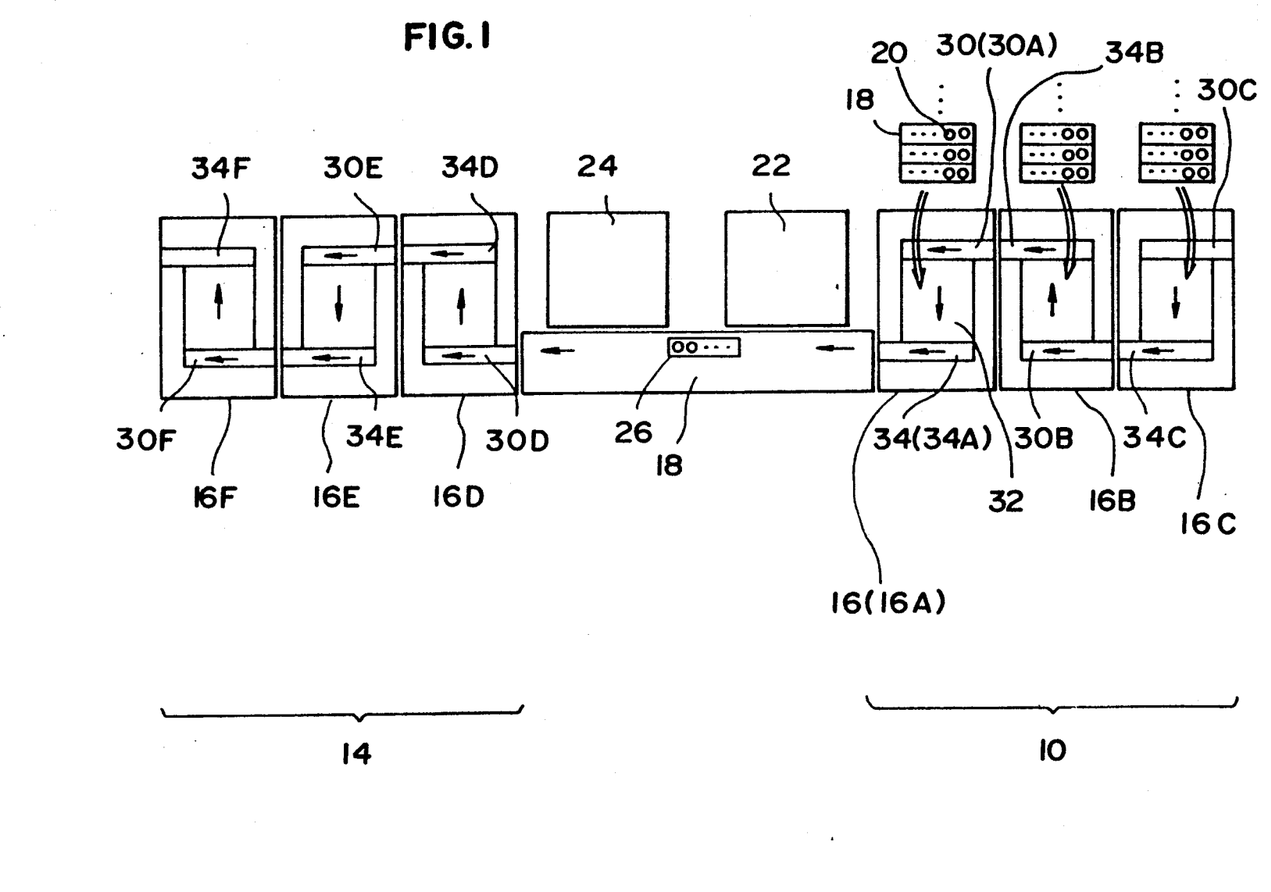
FIG. 1 is a plan view showing an embodiment of a sampler for many samples according to the invention.

As shown in FIG. 1, a sampler for many samples according to comprises a rack start yard 10, a conveyor 12, and a rack stock yard 14. Numeral 18 is a sample rack mounting a plurality of sample containers 20. A plurality of sample racks 18 are set in the rack start yard 10. The sample racks 18 are put on the conveyor one by one, and are presented to blood analyzers 22, 24. Before the blood analyzers 22, 24, the sample racks 18 are transferred intermittently, and samples for one specimen each are taken. The sample racks after sampling are recovered in the rack stock yard 14.

Rack start/stock units 16 are used in the rack start yard 10 and rack stock yard 14. The rack start/stock units 16 possess the function of taking in the sample racks 18 from outside the equipment, and sending out the sample racks 18 to the outside of the equipment. A loader 30 loads the sample racks 18 in the longitudinal direction. An unloader 34 unloads the sample racks 18 in the longitudinal direction. Between the loader 30 and the unloader 34, there is an accumulator 32 in which plural sample racks may be arranged in plural rows.

In FIG. 1, three rack start/stock units 16A, 16B, 16C are used in the rack start yard 10. An unloader 34A of the first rack start/stock unit 16A is connected to the conveyor 12, and its loader 30A to the unloader 34B of the second rack start/stock unit 16B. The loader 30B of the second rack start/stock unit 16B is connected to the unloader 34C of the third rack start/stock unit 16C. Similarly, three rack start/stock units 16D, 16E, 16F are used in the rack stock yard 14. A loader 30D of the fourth start/stock unit 16D is connected to the conveyor 12, and its unloader 34D is connected to the loader 30E of the fifth rack start/stock unit 16E. The unloader 34E of the fifth rack start/stock unit 16E is connected to the loader 30F of the sixth rack start/stock unit 16F.

Supposing 20 sample racks can be set at once on the accumulator of one rack start/stock unit, a total of 60 sample racks can be set at once in this embodiment.

Figure 2:
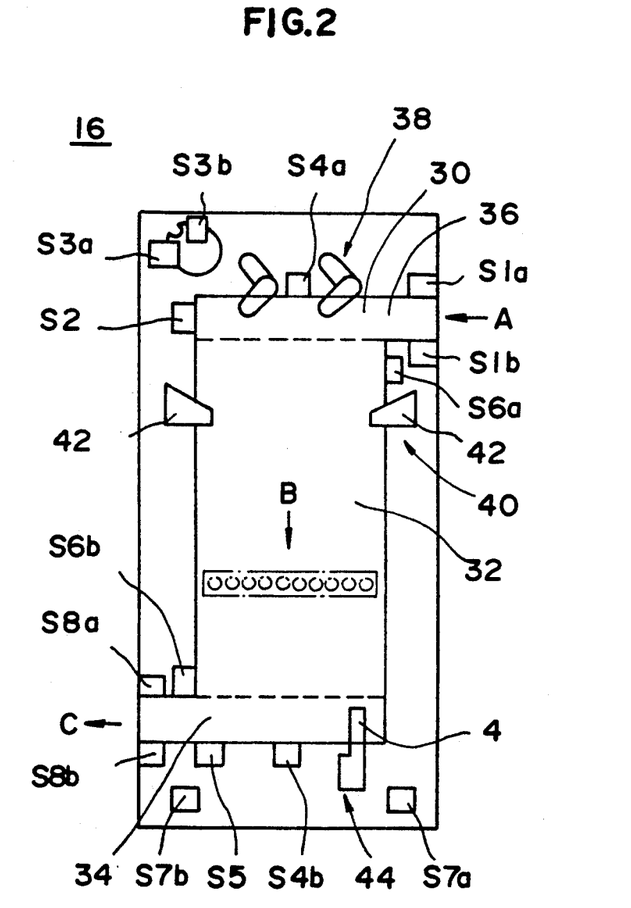
Figure 3:
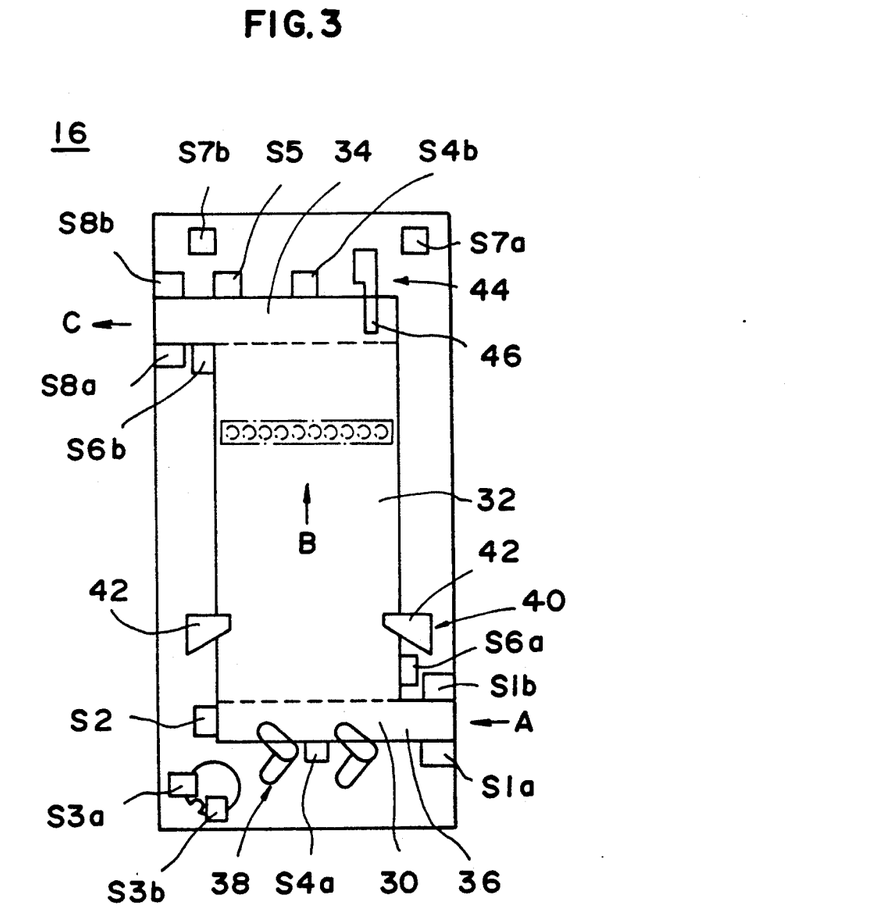

FIG. 2 and FIG. 3 are schematic plan views of the rack start/stock unit 16. The construction and function are the same although the configuration and direction are different. FIG. 2 shows to the first, third and fifth rack start/stock units 16A, 16C, 16E, while FIG. 3 shows the second, fourth and sixth rack start/stock units 16B, 16D, 16F.

The operation is explained below. In the first place, sample racks are sent into the loader 30 in the arrow A direction. At this time, sensors S1a, S1b detect that the sample racks have been sent in.

Next, the belt 36 of the loader 30 rotates, and the sample racks are moved deeper into the of the loader 30. The sensor S2 detects that the sample racks have the maximum depth of the loader 30.

The introduced rack is then pushed into the accumulator 32 by a first moving means 38. The moving range of the first moving means is determined by sensors S3a, S3b. Whether a sample rack is present or not in the accumulator 32 is detected by the sensors S4a, S4b.

The second moving means 40 operates, and the sample rack pushed into the accumulator 32 is moved in the direction of arrow B (the lever 42 pushes the sample rack, and the moving range of the lever 42 is determined by sensors S6a, S6b). By the second moving means 40, the sample racks in the accumulator 32 are entirely moved in the direction of arrow B.

Of the sample racks in the accumulator 32, when the first sample rack reaches the unloader 34, it is detected by the sensor S5.

In succession, the third moving means 44 operates, and the sample rack on the unloader 34 is pushed by the lever 46 to move in the direction of arrow C. The moving range of the lever 46 is determined by the sensors S7a, S7b. When the sample rack is pushed out by the unloader 34, it is detected by the sensors S8a, S8b.

Meanwhile, the sensors S1a and S1b, S4a and S4b, and S8a and S8b are respectively transmitters and receivers of a light transmission type sensor. On the other hand, the sensors S2, S5, S6a, S7a, S7b are microswitches, and sensors S3a, S3b, S6b are photo interruptors.

Figure 4:
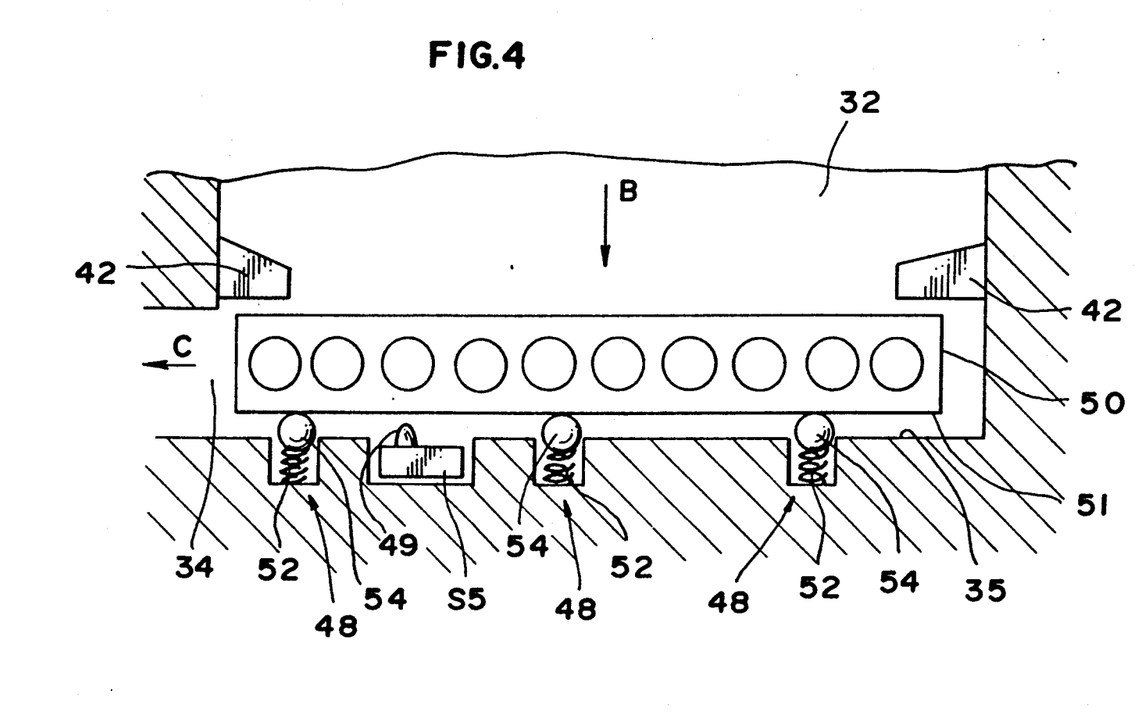
FIG. 4 is a detailed plan view around the unloader of the rack start/stock unit shown in FIG. 2.

FIG. 4 is a plan view of the unloader 34 portion for explaining the sensor S5. On the unloader wall 35, push-back means 48 for pushing back the sample rack and the sensor S5 are attached. By the lever 42 of the second moving means, the front side 51 of the sample rack 50 pushed to the unloader wall 35 in the direction of arrow B overcomes the force of the spring 52 of the push-back means 48, and tightly contacts the unloader wall 35, and pushes the actuator 49 of the sensor S5 to turn on the sensor S5.

When the lever 42 of the second moving means returns to the home position, the spring 52 of the push-back means 48 is restored, and the sample rack is pushed back by a specific distance (1 to 2 mm), and the sensor S5 is turned off. Numeral 54 is a ball-shaped member.

Figure 5:
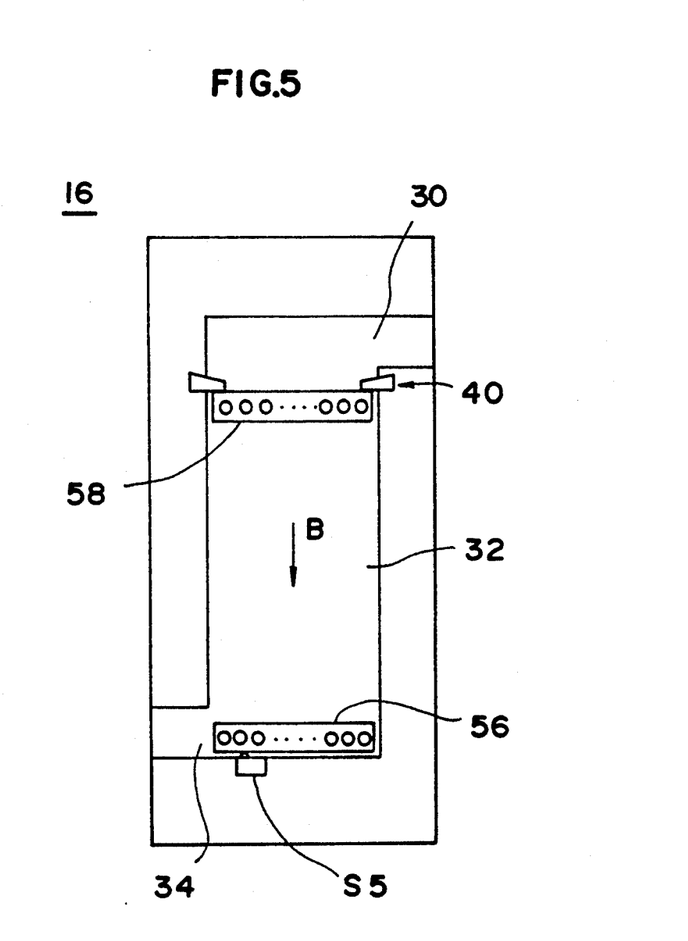
FIG. 5 shows a plan view of the rack start/stock unit without push-back means.

The purpose of disposing the push-back means 48 for pushing back the sample rack in the sensor S5 portion is explained below. In FIG. 5, in the absence of a sample rack, the sensor S5 is turned off. When a first sample rack 56 is sent to the accumulator 32, the second moving means 40 operates until the sensor S5 is turned on (that is, until the sample rack 56 reaches the unloader 34). Next, the second sample rack 58 is sent into the accumulator 32. However, since the sensor S5 remains in the ON state, the second moving means 40 does not operate. That is, the sample rack 56 in the unloader and the sample rack 58 newly pushed into the accumulator 32 are not brought into mutual contact.

Figure 6:
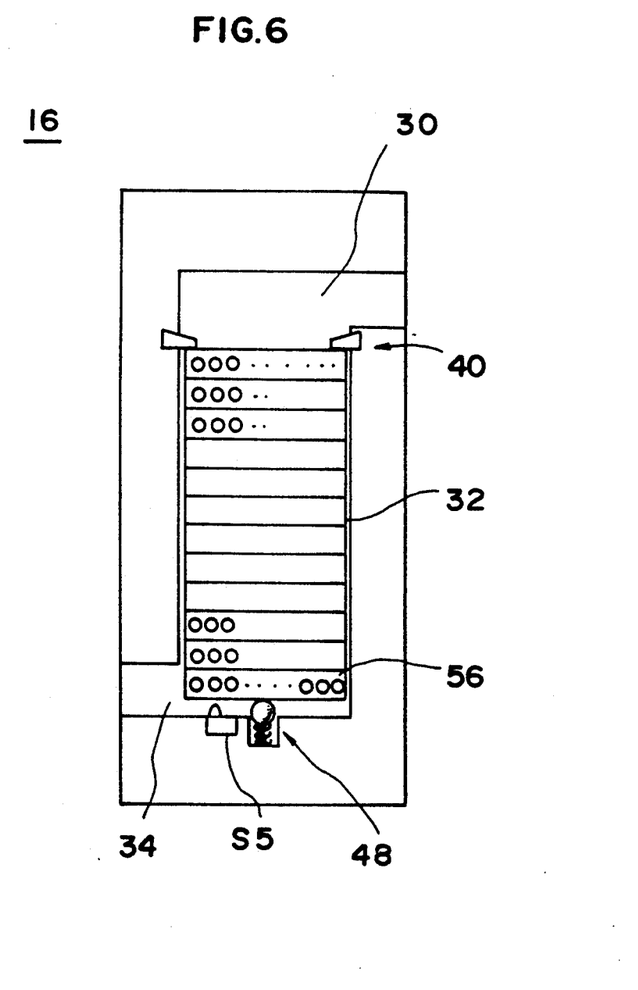
FIG. 6 is a plan view of the rack start/stock unit with push-back means.

By using the push-back means 48 as shown in FIG. 4, however, even if the sample rack is present in the unloader 34, the sensor S5 is not turned on as shown in FIG. 6, so that the second moving means 40 operates, thereby bringing the sample racks into mutual contact. When the sample racks contact each other and the sensor S5 is turned on, the second moving means 40 returns to the original position.

Thus, f the sample rack is not sent out from the unloader 34, new sample racks can be taken in until the accumulator 32 is filled up with sample racks.

The first moving means 38 and the second moving means 40 may be known ones as disclosed, for example, in the Japanese Laid-open Utility Models Sho. 63-141456 and Sho. 63-141458. Besides, the third moving means 44 may be also realized by using the known technology.

Figure 7:
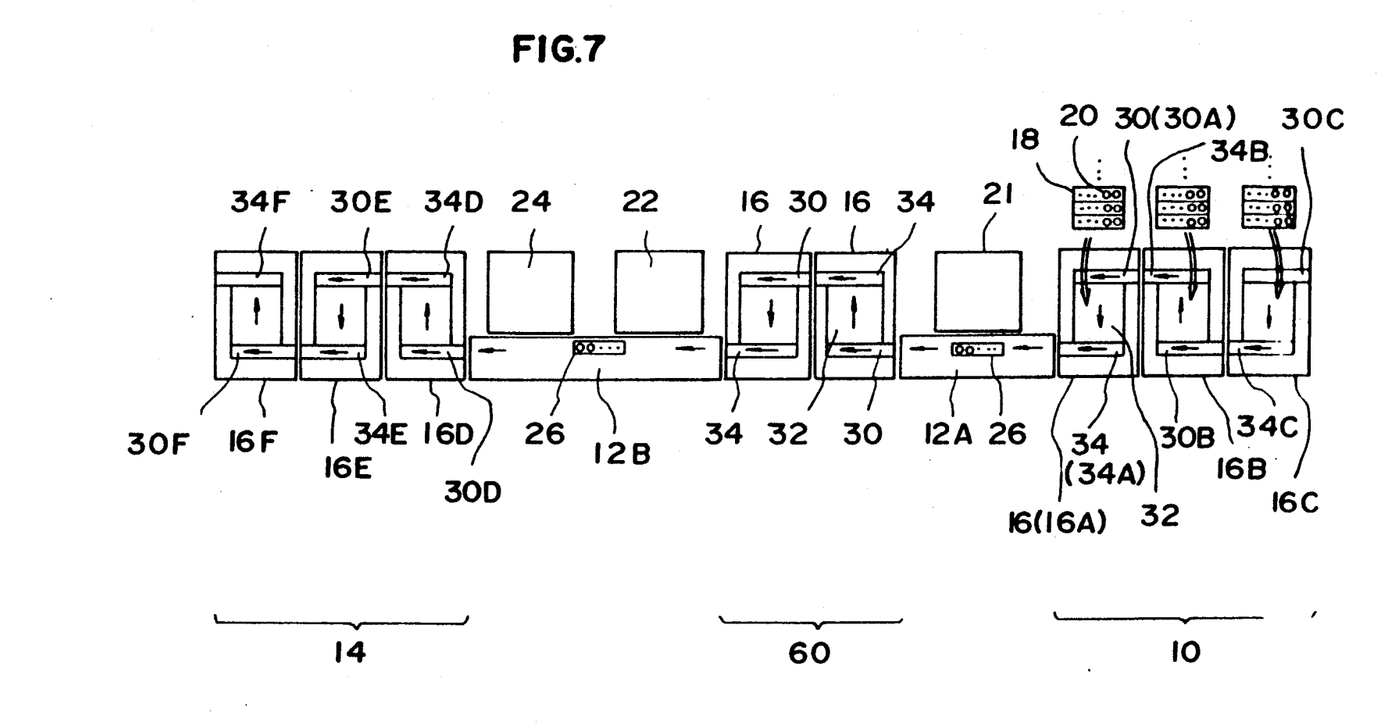
FIG. 7 is a plan view showing another embodiment of a sampler for many samples according to the invention.

FIG. 7 shows a different embodiment of the invention. In this embodiment, between the conveyor 12a and conveyor 12B, a cushion yard (rack pooler) 60 is installed. The cushion yard 60 comprises one or plural rack start/stock units 16, intened to convey the racks without having to cause the high speed analyzer to wait, thereby keeping the racks stagnant, when connecting plural analyzers 21, 22, 24 differing in processing capacity.

The sampler for many samples of this embodiment comprises a rack start yard 10, conveyors 12A, 12B, cushion yard 60, and rack stock yard 14. Numeral 18 is a sample rack in which plural sample containers 20 are installed. A plurality of sample racks 18 are set on the rack start yard 10. The sample racks 18 are sent into the conveyor 12A one by one, and are presented for a blood analyzer 21. Before the analyzer 21, the sample racks 26 are transferred intermittently, and samples are taken for each specimen. The sample racks after sampling are sent into the cushion yard 60.

In this embodiment, the cushion yard 60 consists of plural (two in the example in FIG. 7) rack start/stock units 16, the loader 30 of the upstream side rack start/stock unit, the upstream side conveyor 12A, which communicate with each other, the unloader 34 of the downstream side rack start/stock unit, the downstream side conveyor 12B, which communicate with each other, the loader 30 of the downstream side rack start/stock unit and the unloader 34 of the upstream side rack start/stock unit, which communicate with each other, by connecting the rack start/stock units in series.

Meanwhile, three or more rack start/stock units may be required, and the number of units is determined by the stagnant state of the racks.

From the cushion yard 60, the racks are sent into the conveyor 12B, and are presented for the blood analyzers 22, 24. Before the analyzers 22, 24, the sample racks 26 are conveyed intermittently, and a sample is taken by one specimen each. After sampling the racks are recovered in the rack stock yard 14.

In this embodiment, if the processing speed of the upstream side analyzer 21 is fast and that of the downstream side analyzers 22, 24 is slow, the loss time can be eliminated. That is, the high speed analyzer can process at high speed regardless of the processing capacity of the low speed analyzers.

Or if some trouble occurs in the upstream side analyzer 21 to cause a temporary stop, it is not necessary to stop the entire system. In this case, the cushion yard 60 functions as the rack start yard, so that processing may be done by the downstream side analyzers 22, 24. That is, the down time of the system is eliminated.

On the contrary, if the downstream side analyzer 22 or/and 24 should be stopped, the cushion yard 60 may function as the rack stock yard, so that processing may be continued by the upstream side analyzer 21.

This explanation refers to a case of three analyzers, but the same holds true if two, or four or more analyzers are used.

Figure 8:
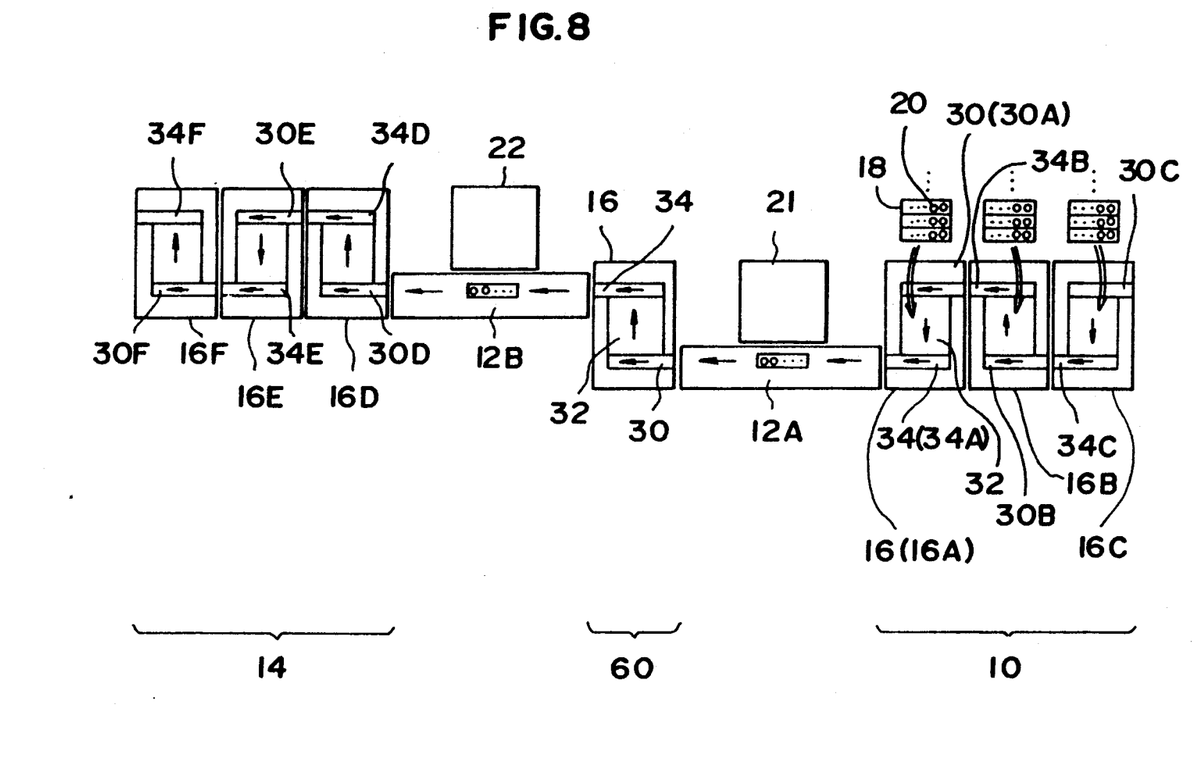
FIG. 8 is a plan view showing still another embodiment of a sampler for many samples according to the invention.

FIG. 8 shows a further different embodiment of the invention. In this embodiment, the cushion yard 60 consists of one rack start/stock unit. That is, the loader 30 of the rack start/stock unit 16 and the upstream side conveyor 12A communicate with each other, and its unloader 34 and the downstream side conveyor 12B communicate with each other.

Embodied and as described herein, the invention brings about the following effects.

(1) Since the rack start yard and rack stock yard are composed by connecting plural rack start/stock units in series, the rack start yard and rack stock yard differing in the number of racks may be easily composed by varying the number of units connected. It is also possible to easily extend this arrangement. Moreover, the manufacturing cost is low.

(2) If any one of the rack start/stock units experience trouble, the other rack start/stock units can act as a substitute, so that system shutdown is avoided.

(3) When the sensor and push-back means of a sample rack are attached to the wall of the unloader, if sample racks are not sent out from the unloader, new sample racks can be accepted until the accumulator is filled up with sample racks.

(4) When installing a cushion yard comprising at least one rack start/stock unit between conveyors, plural sample racks may be temporarily held and kept. Accordingly, when connecting plural analyzers having different processing capacities, the high speed analyzer can process at high speed regardless of the processing capacity of the low speed analyzers, by forming a stagnant flow of racks. Besides, if the upstream side analyzer is stopped, the cushion yard functions as the rack start yard, so that processing may be done by the downstream side analyzer. Likewise, if the downstream size analyzer is stopped, the cushion yard functions as the rack stock yard, and processing may be done by the upstream side analyzer.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A sampler for sequentially handling a plurality of sample racks, comprising:
    a rack start yard;
    a conveyor;
    at least one analyzer;
    a rack stock yard, said conveyor connecting said rack start yard and rack stock yard to each other and to said at least one analyzer; and
    at least first and second rack start/stock units arranged symmetrically to each other, said rack start yard and said rack stock yard being formed by mutually connecting the rack start/stock units, wherein:
    each rack start/stock unit comprises: a loader for loading sample racks from outside of the unit; an accumulator for accumulating a plurality of sample racks, said accumulator being contiguous to the loader; an unloader unit, said unloader being contiguous to said accumulator; first moving means for moving the sample racks from the loader to the accumulator; second moving means for moving the sample racks in the accumulator to the unloader; and third moving means for moving the sample racks at the unloader outside of the unit;
    the unloader of the most downstream rack start/stock unit in the start yard is connected to the conveyor;
    the loader of the most upstream rack start/stock unit in the stock yard is connected to the conveyor; and
    in the start yard and stock yard, adjacent rack start stock units are situated such that the loader of a certain rack start/stock unit communicates with the unloader of another rack start/stock unit.

2. The sampler as defined in claim 1, wherein each rack start/stock unit further comprises: a sensor; and push-back means for pushing back the sample racks engaging the wall of the loader, wherein:
    the sensor turns to an ON state when the sample rack contacts the wall of the unloader and to an OFF state when the sample rack disengages the wall of the unloader; and
    the push-back means pushes the sample rack back from the wall of the unloader by a specific distance and with a specific force, such that the sensor turns to its OFF state.

3. A sampler for sequentially handling a plurality of sample racks, comprising:
    a rack start yard;
    a conveyor;
    at least one analyzer;
    a rack stock yard, said conveyor connecting said rack start yard and rack stock yard to each other and to said at least one analyzer;
    at least first and second rack start/stock units arranged symmetrically to each other, said rack start yard and said rack stock yard being formed by mutually connecting the rack start/stock units; and
    a cushion yard disposed between the start yard and the stock yard and in association with the conveyor, said cushion yard being formed by temporarily mutually connecting rack start/stock units, wherein:
    each rack start/stock unit comprises: a loader for loading sample racks from outside of the unit; an accumulator for accumulating a plurality of sample racks, said accumulator being contiguous to the loader; an unloader unit, said unloader being contiguous to said accumulator; first moving means for moving the sample racks from the loader to the accumulator; second moving means for moving the sample racks in the accumulator to the unloader; and third moving means for moving the sample racks at the unloader outside of the unit;
    the unloader of the most downstream rack start/stock unit in the cushion yard is connected to the conveyor;
    the loader of the most upstream rack start/stock unit in the cushion yard is connected to the conveyor; and
    in the start yard and stock yard, adjacent rack start stock units are situated such that the loader of a certain rack start/stock unit communicates with the unloader of another rack start/stock unit.

4. The sampler as defined in claim 3, wherein each rack start/stock unit further comprises: a sensor; and push-back means for pushing back the sample racks engaging the wall of the loader, wherein:
    the sensor turns to an ON state when the sample rack contacts the wall of the unloader and to an OFF state when the sample rack disengages the wall of the unloader; and
    the push-back means pushes the sample rack back from the wall of the unloader by a specific distance and with a specific force, such that the sensor turns to its OFF state.

5. The sampler as defined in claim 3, wherein:
    when the cushion yard has a plurality of rack start/stock units the loader of the most upstream rack start/stock unit and the most upstream conveyor communicate with each other, and the unloader of the most downstream rack start/stock unit and the most downstream conveyor communicate with each other; and
    that for adjacent rack start/stock units the loader of a certain rack start/stock unit and the unloader of the other rack start/stock unit may communicate with each other.

6. A rack start/stock unit for a sampler for sequentially holding a plurality of sample racks, comprising:

a loader for loading sample racks from outside the unit;

an accumulator for accumulating a plurality of sample racks, said accumulator being contiguous to the loader;

an unloader for moving sample racks outside of the unit said unloader being contiguous to said accumulator;

first moving means for moving the sample racks from the loader to the accumulator;

second moving means for moving the sample racks in the accumulator to the unloader;

third moving means for moving the sample racks at the unloader outside of the unit;

a sensor; and push-back means for pushing back the sample racks engaging the wall of the unloader; wherein:

the sensor turns to an ON state when the sample rack contacts the wall of the unloader and to an OFF state when the sample rack disengages the wall of the unloader; and the push-back means pushes the sample rack back from the wall of the unloader by a specific distance and with a specific force, such that the sensor turns to its OFF state.

* * * * *